(12) United States Patent
Al-Ali et al.

(10) Patent No.: US 9,138,182 B2
(45) Date of Patent: *Sep. 22, 2015

(54) OPTICAL SENSOR INCLUDING DISPOSABLE AND REUSABLE ELEMENTS

(71) Applicant: Cercacor Laboratories, Inc., Irvine, CA (US)

(72) Inventors: Ammar Al-Ali, San Juan Capistrano, CA (US); Yassir Abdul-Hafiz, Irvine, CA (US); Eric Yang, Irvine, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/066,529

(22) Filed: Oct. 29, 2013

(65) Prior Publication Data

US 2014/0128699 A1 May 8, 2014

Related U.S. Application Data

(63) Continuation of application No. 12/829,276, filed on Jul. 1, 2010, now Pat. No. 8,600,467, which is a continuation-in-part of application No. 11/606,455, filed on Nov. 29, 2006, now Pat. No. 8,233,955.

(60) Provisional application No. 61/222,450, filed on Jul. 1, 2009.

(51) Int. Cl.
*A61B 5/1455* (2006.01)
*A61B 5/00* (2006.01)
*A61B 5/024* (2006.01)

(52) U.S. Cl.
CPC ......... *A61B 5/14551* (2013.01); *A61B 5/14552* (2013.01); *A61B 5/6826* (2013.01);

(Continued)

(58) Field of Classification Search
CPC ..................................................... A61B 5/1455
USPC ................................................... 600/310–344
See application file for complete search history.

(56) References Cited

U.S. PATENT DOCUMENTS 3,229,823 A    1/1966  Hummer
3,631,821 A    1/1972  Zachariou (Continued)

FOREIGN PATENT DOCUMENTS

AU        745306        3/2002
CA     2 346 639        4/2000

(Continued)

OTHER PUBLICATIONS

European Office Action dated Sep. 27, 2011 in EP Application No. 06 838 888.3.

(Continued)

*Primary Examiner* — Eric Winakur
*Assistant Examiner* — Marjan Fardanesh
(74) *Attorney, Agent, or Firm* — Knobbe, Martens, Olson & Bear LLP

(57) ABSTRACT

An embodiment of the present disclosure provides a noninvasive optical sensor or probe including disposable and reusable components. The assembly of the disposable and reusable components is straightforward, along with the disassembly thereof. During application to a measurement site, the assembled sensor is advantageously secured together while the componentry is advantageously properly positioned.

18 Claims, 14 Drawing Sheets

(52) U.S. Cl.
CPC .......... *A61B5/6838* (2013.01); *A61B 5/02427* (2013.01); *A61B 2562/085* (2013.01); *A61B 2562/12* (2013.01); *Y10T 29/49002* (2015.01)

(56) References Cited

U.S. PATENT DOCUMENTS

| | | | |
|---|---|---|---|
| 4,601,247 A | 7/1986 | Welch et al. | |
| 4,621,643 A | 11/1986 | New, Jr. et al. | |
| 4,685,464 A | 8/1987 | Goldberger et al. | |
| 4,700,708 A | 10/1987 | New, Jr. et al. | |
| 4,830,014 A | 5/1989 | Goodman et al. | |
| 4,865,038 A | 9/1989 | Rich et al. | |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,090,410 A | 2/1992 | Saper et al. | |
| 5,094,240 A | 3/1992 | Muz | |
| 5,158,323 A | 10/1992 | Yamamoto et al. | |
| 5,163,438 A | 11/1992 | Gordon et al. | |
| 5,170,786 A | 12/1992 | Thomas et al. | |
| 5,209,230 A | 5/1993 | Swedlow et al. | |
| 5,249,576 A | 10/1993 | Goldberger et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| 5,387,122 A | 2/1995 | Goldberger et al. | |
| D359,546 S | 6/1995 | Savage et al. | |
| 5,431,170 A | 7/1995 | Mathews | |
| D361,840 S | 8/1995 | Savage et al. | |
| 5,437,275 A | 8/1995 | Amundsen et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,507,286 A | 4/1996 | Solenberger | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,619,992 A | 4/1997 | Guthrie et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,660,567 A | 8/1997 | Nierlich et al. | |
| 5,664,270 A | 9/1997 | Bell et al. | |
| 5,673,693 A | 10/1997 | Solenberger | |
| 5,678,544 A | 10/1997 | DeLonzor et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,817,008 A | 10/1998 | Rafert et al. | |
| 5,817,010 A | 10/1998 | Hibl | |
| 5,823,950 A | 10/1998 | Diab et al. | |
| 5,830,131 A | 11/1998 | Caro et al. | |
| 5,833,618 A | 11/1998 | Caro et al. | |
| RE36,000 E | 12/1998 | Swedlow et al. | |
| 5,860,919 A | 1/1999 | Kiani-Azarbayjany et al. | |
| 5,879,373 A | 3/1999 | Röper et al. | |
| 5,890,929 A | 4/1999 | Mills et al. | |
| 5,904,654 A | 5/1999 | Wohltmann et al. | |
| 5,910,108 A | 6/1999 | Solenberger | |
| 5,919,133 A | 7/1999 | Taylor et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,991,648 A | 11/1999 | Levin | |
| 5,995,855 A | 11/1999 | Kiani et al. | |
| 5,997,343 A | 12/1999 | Mills et al. | |
| 5,999,834 A | 12/1999 | Wang et al. | |
| 6,002,952 A | 12/1999 | Diab et al. | |
| 6,011,986 A | 1/2000 | Diab et al. | |
| 6,014,576 A | 1/2000 | Raley | |
| 6,027,452 A | 2/2000 | Flaherty et al. | |
| 6,036,642 A | 3/2000 | Diab et al. | |
| 6,045,509 A | 4/2000 | Caro et al. | |
| 6,061,584 A | 5/2000 | Lovejoy et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada et al. | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,301,493 B1 | 10/2001 | Marro et al. | |
| 6,308,089 B1 | 10/2001 | von der Ruhr et al. | |
| 6,317,627 B1 | 11/2001 | Ennen et al. | |
| 6,321,000 B1 | 11/2001 | King | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,381,489 B1 | 4/2002 | Ashibe | |
| 6,388,240 B2 | 5/2002 | Schulz et al. | |
| 6,397,091 B2 | 5/2002 | Diab et al. | |
| 6,405,910 B1 | 6/2002 | Infanti et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,484 B1 | 2/2003 | Lovejoy et al. | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,585,287 B1 | 7/2003 | Spaulding et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |

(56) References Cited

U.S. PATENT DOCUMENTS

| | | |
|---|---|---|
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Kollias et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Al et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,240,803 B2 | 7/2007 | Stitchick et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |

(56) References Cited

U.S. PATENT DOCUMENTS

| | | | |
|---|---|---|---|
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,856 B2 | 6/2014 | Diab et al. |
| 8,755,872 B1 | 6/2014 | Marino |
| 8,761,850 B2 | 6/2014 | Lamego |
| 8,764,671 B2 | 7/2014 | Kiani |

(56) References Cited

U.S. PATENT DOCUMENTS

| | | | |
|---|---|---|---|
| 8,768,423 B2 | 7/2014 | Shakespeare et al. |
| 8,771,204 B2 | 7/2014 | Telfort et al. |
| 8,781,549 B2 | 7/2014 | Al-Ali |
| 8,868,150 B2 | 10/2014 | Al-Ali et al. |
| 2001/0029325 A1 | 10/2001 | Parker |
| 2001/0045532 A1 | 11/2001 | Schulz et al. |
| 2002/0156353 A1 | 10/2002 | Larson |
| 2003/0009092 A1 | 1/2003 | Parker |
| 2005/0145588 A1 | 7/2005 | Stitchick et al. |
| 2005/0184895 A1 | 8/2005 | Petersen et al. |
| 2013/0023743 A1 | 1/2013 | Al-Ali |
| 2014/0330099 A1 | 11/2014 | Al-Ali |

FOREIGN PATENT DOCUMENTS

| | | |
|---|---|---|
| CA | 2 366 493 A1 | 11/2002 |
| EP | 1 222 894 A2 | 7/2002 |
| EP | 1 222 894 A3 | 7/2002 |
| EP | 1956968 | 8/2008 |
| EP | 2374407 | 11/2011 |
| JP | 2003-521985 | 7/2003 |
| JP | 2004-329406 | 11/2004 |
| JP | 5049289 | 7/2012 |
| JP | 5575181 | 7/2014 |
| WO | WO 00/21433 | 4/2000 |
| WO | WO 02/89664 | 4/2000 |
| WO | WO 01/03574 A1 | 1/2001 |
| WO | WO 2007/064984 | 6/2007 |

OTHER PUBLICATIONS

Extended European Search Report dated Sep. 12, 2011 in EP Application No. 11169443.6.
International Search Report for PCT/US2006/007516, filed Mar. 1, 2006, in 4 pages.
International Search Report for PCT/US2006/046176, filed Nov. 29, 2006, in 5 pages.
Japanese Office Action dated Feb. 22, 2012 in JP Application No. 2008-543525.
Schmitt, Joseph M.; et al. "Measurement of Blood Hematocrit by Dual-wavelength Near-IR Photoplethysmography", published May 1992, Proc. SPIE vol. 1641, p. 150-161, Physiological Monitoring and Early Detection Diagnostic Methods, Thomas S. Mang; Ed. (SPIE homepage), in 12 pages.
Japanese Office Action dated Dec. 3, 2013 in JP Application No. 2012-120877.
PCT International Search Report, App. No. PCT/US2006/046176, App. Date: Nov. 29, 2006, 4 pages.

OPTICAL SENSOR INCLUDING DISPOSABLE AND REUSABLE ELEMENTS

CROSS-REFERENCE TO RELATED APPLICATIONS

This application claims priority benefit under 35 U.S.C. §119(e) to U.S. Provisional Patent Application Ser. No. 61/222,450, filed Jul. 1, 2009 and is a continuation of U.S. application Ser. No. 12/829,276, filed Jul. 1, 2010, published as U.S. Patent Application Publication No. 2011/0004079, which is a continuation-in-part of U.S. application Ser. No. 11/606,455, filed Nov. 29, 2006, published as U.S. Patent Application Publication No. 2007/0123763. The disclosures of each of the priority applications are incorporated by reference herein. Additionally, this application relates to U.S. Pat. No. 6,920,345, issued Jul. 19, 2005, U.S. Pat. No. 7,225,007, issued May 29, 2007, U.S. application Ser. No. 11/754,972, filed May 29, 2007, published as U.S. Patent Application Publication No. 2007/0244378, and U.S. application Ser. No. 11/606,455, filed Nov. 29, 2006, published as U.S. Patent Application Publication No. 2007/0123763, the disclosures of which are incorporated in their entirety by reference herein.

FIELD OF THE DISCLOSURE

The present disclosure relates to noninvasive optical sensors capable of detecting light attenuated by body tissue. More specifically, the disclosure relates to the combination of reusable and disposable components of such sensors.

BACKGROUND OF THE DISCLOSURE

Early detection of low blood oxygen is important in a wide range of applications, including patient monitoring, the fitness industry, home care and the like. Noninvasive oximetry was developed to study and to measure, among other things, the oxygen status of blood. Pulse oximetry—a noninvasive, widely accepted form of oximetry—relies on a sensor attached externally to a patient to output signals indicative of various physiological parameters, such as a patient's blood oxygen saturation.

A pulse oximeter sensor generally includes one or more energy emission devices, such as specific wavelength emitting LEDs, and one or more energy detection devices. The sensor is generally attached to a measurement site such as a patient's finger, ear, ankle, or the like, using an attachment mechanism such as a disposable tape, reusable housing, a plastic or hook-and-loop fastening strap, or the like. The attachment mechanism positions the emitters and detector proximal to the measurement site such that the emitters project energy into the blood vessels and capillaries of the measurement site, which in turn attenuate the energy. The detector then detects that attenuated energy. The detector communicates at least one signal indicative of the detected attenuated energy to a signal processing device such as an oximeter. The oximeter generally calculates, among other things, one or more physiological parameters of the measurement site.

High fidelity pulse oximeters capable of reading through motion induced noise are disclosed in U.S. Pat. Nos. 6,770,028, 6,658,276, 6,157,850, 6,002,952 5,769,785, and 5,758,644, which are assigned to Masimo Corporation ("Masimo") and are incorporated by reference herein. Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt), total Hematocrit (Hct), oxygen concentrations and glucose concentrations, as a few examples. Advanced physiological monitors and corresponding multiple wavelength optical sensors capable of measuring parameters in addition to $SpO_2$, such as HbCO, HbMet and Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Laboratories, Inc. and incorporated by reference herein. Further, noninvasive blood parameter monitors and corresponding multiple wavelength optical sensors, such as Rainbow™ adhesive and reusable sensors and RAD-57™ and Radical-7™ monitors for measuring $SpO_2$, pulse rate, perfusion index (PI), signal quality (SiQ), pulse variability index (PVI), HbCO and HbMet, among other parameters, are also available from Masimo.

Noninvasive oximetry sensors can be disposable, reusable, or some combination thereof. Reusable sensors offer advantages of superior cost savings. However, reusable sensors are often available in a limited number of sizes even though patient measurement sites, such as fingers or toes, can have a much larger size distribution. Therefore, sometimes reusable sensors do not readily conform to each patient's attachment site. Disposable sensors on the other hand offer superior conformance to the measurement area. However, disposable sensors are generally more costly due to limited use of the relatively expensive sensor components which could otherwise last for repeated uses.

Faced with the drawbacks of reusable and disposable sensors, manufacturers began designing a number of middle-ground sensors. For example, some manufacturers offer a reusable detector portion that couples to a disposable emitter portion. After a single use, the disposable emitter portion is detached from the reusable detector portion and discarded. While this design reuses some of the expensive electronic components, others are still discarded.

Another example of a middle-ground sensor includes a reusable "Y" type sensor, where a reusable emitter portion connects to one branch of the "Y" while a reusable detector portion connects to the other branch. A disposable tape positions the two branches on a measurement site. In this design, the electronics are reusable; however, the multiple wires tend to be somewhat difficult to properly attach, especially with a moving patient.

Other examples of middle-ground sensors include a disposable tape sandwich where a reusable flexible circuit housing an emitter portion and a detector portion, are "sandwiched" between adhesive layers. Separation of such disposable tape sandwiches can be cumbersome. In yet another example of a middle-ground sensor, the Assignee of the present application disclosed a reusable flexible circuit is snapped into a disposable tape. In an embodiment of that disclosure, small pegs on the flexible circuit snap into mechanically mating elements on the disposable tape. Grooves allow some longitudinal travel between the reusable portion and the disposable portion, thereby allowing for some self adjustment between components to account for differences in radial attachment requirements.

SUMMARY OF THE DISCLOSURE

However, even with the advances discussed in the foregoing, there continues to be a need for a commercially viable, straightforward, middle-ground solution that offers reusability of expensive electronic components while maintaining some of the advantages of disposable attachment.

Accordingly, one aspect of an embodiment of the present disclosure is to provide a sensor having reusable and disposable components. In an embodiment, the sensor advantageously includes a disposable component structured to provide a locking feature capable of reducing a chance that the disposable and reusable components can separate when attached or otherwise in close proximity to the body. In an embodiment, a locking mechanism takes advantage of longitudinal displacement to engage when the reusable and disposable portions of the sensor are curved around the measurement site (such as a finger). Separation of the reusable portion from the disposable portion is then advantageously complicated until the sensor is removed from the patient and the displacement is reversed.

A further aspect of an embodiment of this disclosure is that the a portion of the reusable sensor component, such as, for example, the front portion or casing of the reusable sensor component can be attached to and released from a corresponding front housing component on the disposable component substantially vertically, substantially horizontally, or angularly. As such, for example, the front casing of the reusable sensor can attach to and release from the disposable component via the underside of the front casing (e.g., due to upward pulling by the patient or medical personnel), the front of the casing (e.g., due to lateral pulling) or angularly through a portion of both the underside and the front of the casing. This configuration allows for efficient, straightforward mating and separation of the reusable and disposable sensor components. Moreover, strain on the connection between the front portion of the reusable sensor component and the front housing of the disposable component, such as strain due to pulling by the patient or medical personnel, is also advantageously reduced.

In a further embodiment, a memory device or information element is provided as part of the disposable housing. An electrical contact is made between the memory device and the reusable components to, for example, ensure quality control in the disposable housing, provide information to the patient monitor about the type of sensor, type of patient, type of attachment mechanism or attachment position, information about operating characteristics of the sensor, product manufacture or sale history, distributor history, amount of use, combinations of the same or the like.

For purposes of summarizing the disclosure, certain aspects, advantages and novel features of the disclosure have been described herein. Of course, it is to be understood that not necessarily all such aspects, advantages or features will be embodied in any particular embodiment of the disclosure.

BRIEF DESCRIPTION OF THE DRAWINGS

The following drawings and the associated descriptions are provided to illustrate embodiments of the present disclosure and do not limit the scope of the claims.

DETAILED DESCRIPTION

Figure 1:
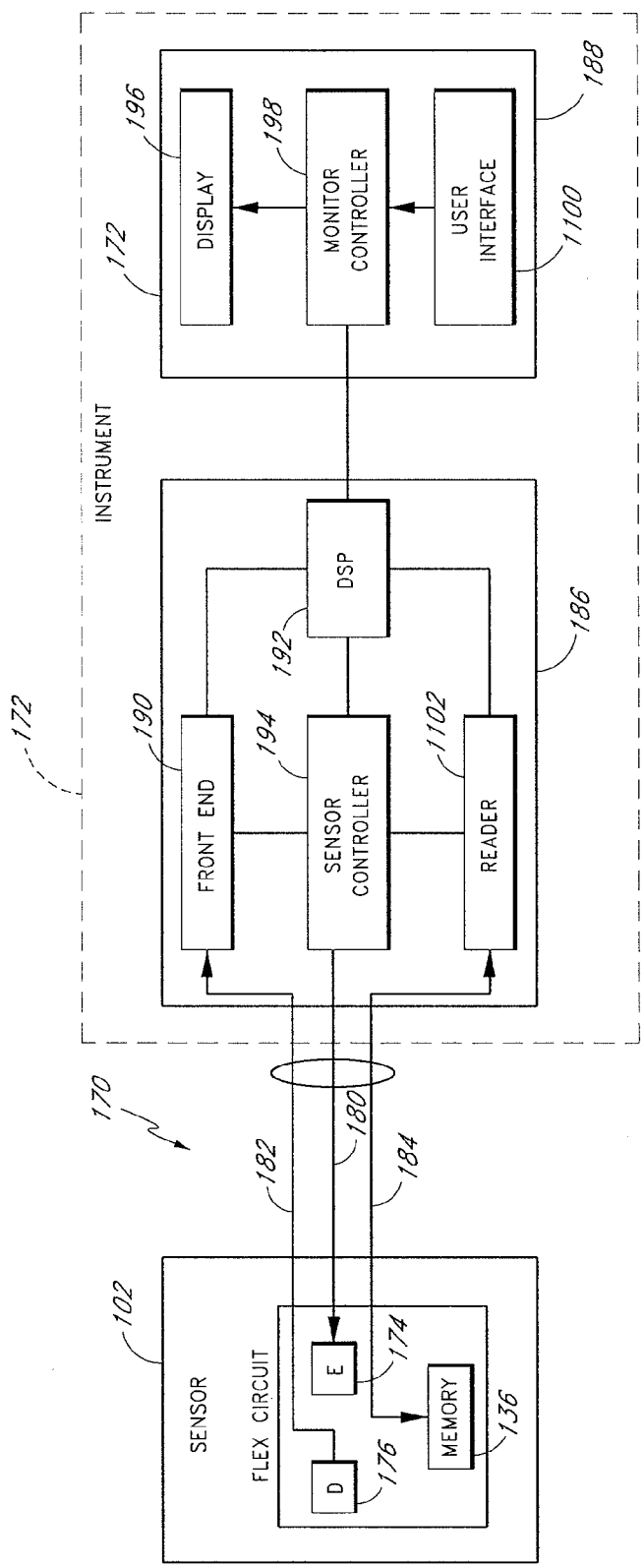
FIG. 1 illustrates an exemplary block diagram of an oximeter system including a sensor and a monitoring instrument, according to embodiments of the disclosure.

An embodiment of the present disclosure is a sensor with a reusable component and a disposable component. The reusable component generally includes reusable relatively expensive electronic components of a sensor, including, for example, the emitters and detector(s). In an embodiment, the emitters and the detector(s) are located in respective casings connected by a short flexible circuit. In an embodiment, a disposable component includes mechanically matable portions adapted to mechanically mate with the casings of the reusable component. In an embodiment, the casings of the reusable component mate with the disposable component in a manner that provides an assembly/disassembly state, and an attached state. During the assembly/disassembly state, a caregiver can readily and straightforwardly assemble the sensor by aligning the casings on the reusable component and the mechanical housings of the disposable component and snapping or sliding them together. In an embodiment, the forward casing of the reusable component is aligned with the forward clip on the disposable component and snapping occurs by lightly pressing on the components vertically, horizontally, or at an angle while on a flat surface or supported from underneath by, for example, the hand of the assembler. In an embodiment, the rearward housing generally vertically accepts the rearward casing in such a way that the rearward casing can move horizontally with respect to the rearward housing; however, one of the housings, such as, for example, the forward housing or clip accepts the casing in such a way as to keep the forward casing generally immobile, in a fixed position with respect to the housing, during use.

Disassembly is also relatively straightforward, as the caregiver may advantageously laterally pull on the reusable component, and the rearward casing extracts from the mechanically mated housing of the disposable element. Continual lifting and/or lateral pulling then similarly extracts the forward casing from the mechanically mated housing of the disposable element. In an embodiment, the forward casing includes at least one opening which receives and generally snaps onto at least one electrical contact of the forward housing. Moreover, each of the openings can extend along a portion of the underside of the casing and along a portion of the front of the casing. As such, the electrical contacts of the housing can attach to and release from the openings via the underside of the casing (e.g., due to upward pulling by the patient or medical personnel), the front of casing (e.g., due to lateral pulling) or angularly, through a portion of the underside and a portion of the front. The at least one opening of certain embodiments is configured to receive at least one prong of the disposable attachment such that the at least one prong is slidable within the opening during mating of the disposable attachment and the second casing. For example, the at least one opening may comprise a channel extending along one or more surfaces of the second casing, such as along a portion of a bottom surface of the second casing and a portion of the front surface of the second casing. The configurations described above thereby allow for efficient, straightforward attachment and release of the forward casing. Moreover, the risk of strain being placed on the sensor components such as strain to due lateral and/or upward pulling by the patient or medical personnel is advantageously reduced. In an embodiment, the flexible circuit between the forward and rearward casing may be reinforced in order to withstand multiple disassembly stresses or forces occurring from the lifting of the reusable wire. In an embodiment, pressing the disposable portion onto a flat surface while lifting the reusable portion aids in the disassembly process.

disposable portion includes structures designed to attach the sensor to a measurement site. In an embodiment, the disposable portion comprises a flexible tape having an adhesive side capable of removably adhering to the measurement site. In an embodiment where the disposable portion wraps around a measurement site, the act of bending the flexible circuit advantageously causes the assembly/disassembly clip to recess into the mechanically mated portion of the disposable housing, thereby reducing the likelihood of disassembly during application to a measurement site. In an embodiment, the sensor components are locked together through the longitudinal displacement of the clip with respect to the disposable housing. In such an embodiment, a stop diminishes the capacity of the clip to move vertically, thereby locking it into place. In this embodiment, removing the adhesive from the measurement site and straightening the sensor components unlocks the reusable and disposable components.

In an embodiment, the assembly also electrically connects electronic components of the disposable portion with those of the reusable portion. In an embodiment, the disposable portion includes an information element or memory device, such as, for example, a resistor, a single wire addressable memory device, such as those EPROMs or EEPROMs commercially available from Dallas Semiconductor, other memory or processing devices, combinations of the same, or the like. The information element may include data accessibly by an attached patient monitor to accomplish quality control, monitor configuration, sensor use monitoring, combinations of the same, or the like.

Still other advantages of embodiments of the present disclosure include proportionally positioning of the mechanically mating housings to provide for optical alignment between the emitters and detector. Moreover, in embodiments including the disposable tape, the tape may advantageously be scored to assist the caregiver in proper alignment with the body tissue at the measurement site.

To facilitate a complete understanding of the disclosure, the remainder of the detailed description describes the disclosure with reference to the drawings. Corresponding parts refer to corresponding elements and the leading digit indicates the figure in which that element first appears.

General Design

FIG. 1 presents an exemplary block diagram of the components generally found in an oximeter sensor, according to an embodiment. For example, FIG. 1 shows as oximeter system 100 including sensor 102, cable 170, and monitor 172. The sensor 102 includes one or more emitters 174 for irradiating body tissue with light, and one or more detectors 176 capable of detecting the light after attenuation by the tissue. The sensor 102 also includes an information element 136 such as an EPROM. The sensor 102 also includes a plurality of conductors communicating signals; including emitter drive signal conductors 180, detector composite signal conductors 182, and EPROM conductors 184. According to an embodiment, the sensor conductors 180, 182, 184 communicate their signals to and from the monitor 172 through cable 170.

Although disclosed with reference to the cable 170, a skilled artisan will recognize from the disclosure herein that the communication to and from the sensor 106 may advantageously include a wide variety of cables, cable designs, public or private communication networks or computing systems, wired or wireless communications, combinations of the same, or the like.

The information element 136 may comprise an EPROM, an EEPROM, combinations of the same, or the like. In general, the information element 136 may include a read-only device or a read and write device. The information element may advantageously also comprise a resistor, an active network, or any combination of the foregoing. The remainder of the present disclosure will refer to such possibilities as simply an information element for ease of disclosure.

The information element 136 may advantageously store some or all of a wide variety of data and information, including, for example, information on the type or operation of the sensor 104, type of patient or body tissue, buyer or manufacturer information, sensor characteristics including the number of wavelengths capable of being emitted, emitter specifications, emitter drive requirements, demodulation data, calculation mode data, calibration data, software such as scripts, executable code, or the like, sensor electronic elements, sensor life data indicating whether some or all sensor components have expired and should be replaced, encryption information, or monitor or algorithm upgrade instructions or data. The information element 136 may advantageously configure or activate the monitor, monitor algorithms, monitor functionality, or the like based on some or all of the foregoing information. For example, without authorized data accessibly on the information element 136, quality control functions may inhibit functionality of the monitor. Likewise, particular data may activate certain functions while keeping others inactive. For example, the data may indicate a number of emitter wavelengths available, which in turn may dictate the number and/or type of physiological parameters that can be monitored or calculated.

FIG. 1 also shows the monitor 172 comprising one or more processing boards 186 communicating with one or more host instruments 188. According to an embodiment, the board 186 comprises processing circuitry arranged on one or more printed circuit boards capable of being installed in specialized monitoring equipment or distributed as an OEM component for a wide variety of patient monitoring equipment. As shown in FIG. 1, the board 186 includes a front end signal conditioner 190, a sensor controller 194, a digital signal processor or microcontroller 192, and a memory reader 1102. In an embodiment, the processor 192 instructs the sensor controller 194 to output one or more drive signals capable of causing the emitters 174 to activate. The front end 190 receives detector output indicating detection of light from the emitters 174 attenuated by body tissue of the measurement site. The front end 190 conditions the signal and outputs the signal and/or signal data to the processor 192. The processor 192 executes calculations adapted to determine values and/or indications or physiological parameters, trends of the parameters, alarms based on the parameters or the trends or combinations of trends and/or parameters, or the like. In addition, the reader 1102 is capable of retrieving information stored on information element 136. The reader 1102 or the processor 192 may advantageously decrypt such information to the extent desired.

In an embodiment, the host instrument 188, communicates with the processor 192 to receive signals indicative of the physiological parameter information calculated by the processor 192. The host instrument preferably includes one or more display devices 196 capable of providing indicia representative of the calculated physiological parameters of the tissue at the measurement site. Such display devices 196 may be controlled by a monitor controller 198 that accepts signals from processor 192. In an embodiment, monitor controller 198 may also accept signals from user interface 1100. Such signals may be indicative of various display options for configuring the output to display 196. In an embodiment, the host instrument 188 may advantageously be capable of displaying one or more of a pulse rate, plethysmograph data, perfusion quality, signal or measurement quality, values of blood constituents in body tissue, including for example, SpCO, functional or fractional $SpO_2$, or the like. In other embodiments, the host instrument 188 is capable of displaying values for one or more of SpMet, $HbO_2$, Hb, HbCO, HbMet, Hct, blood glucose, bilirubin, or the like. In still additional embodiments, the host instrument 188 is capable of displaying trending data for one or more of the foregoing measured or determined data. Moreover an artisan will realize from the disclosure herein many display options for the data are available.

In an embodiment, the host instrument 188 includes audio or visual alarms that alert caregivers that one or more physiological parameters are falling below predetermined safe thresholds, and may include indications of the confidence a caregiver should have in the displayed data. In further embodiments, the host instrument 188 may advantageously include circuitry capable of determining the expiration or overuse of components of the sensor 102, including for example, reusable elements, disposable elements, or combinations of the same.

Although disclosed with reference to particular embodiment, an artisan will recognize from the disclosure herein many variations of the instrument 172. For example, in a broad sense, the instrument 172 accepts data from the sensor 102, determines values for one or more parameters, trends, alarms or the like, and outputs them to an interface such as a display.

Sensor Configuration

Figure 2:
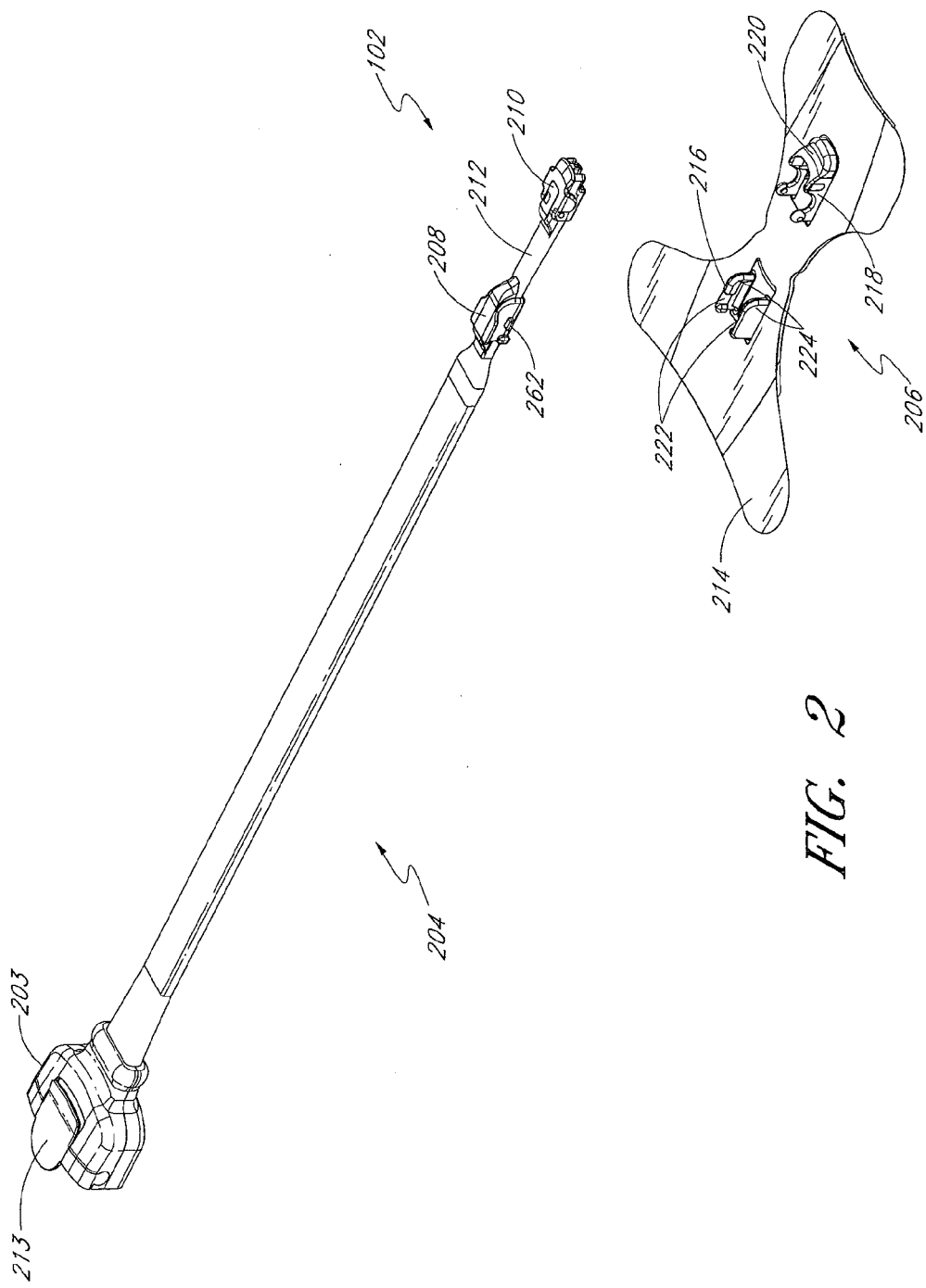
FIG. 2 illustrates a perspective view of the sensor of FIG. 1, where reusable and disposable components of the sensor are separated according to an embodiment of the disclosure.

FIG. 2 illustrates an embodiment of sensor 102, having reusable component 204 and disposable component 206. The components are shown detached. FIG. 3 shows a very similar perspective drawing, but with reusable component 204 and disposable component 206 in their attached, assembled state. Returning to FIG. 2, the reusable component 204 comprises an emitter casing 208, a detector casing 210, and a flexible circuit 212. The emitter casing 208 comprises one or more emission devices (not shown) operable to emit light at multiple wavelengths, such as red and infrared. Detector casing 210 houses one or more detectors (not shown), such as a photodiode detector. In an embodiment, a flexible circuit 212 connects the emitter casing 208 and detector casing 210. In a preferred embodiment, the flexible circuit 212 is housed in a protective cover and extends beyond the emitter casing 208. An artisan will understand from the disclosure herein that the emitter and detector electrical components may advantageously be housed in the casings disclosed or simply reversed from the foregoing disclosure. In an embodiment, the flexible circuit 212 and/or cabling extends significantly beyond the casings to advantageously remove any cable attachment mechanisms from the proximity of the tissue site.

The reusable component 204 of certain embodiments also includes a sensor connector 203 configured to mate with a monitor connector (not shown). The sensor connector 203 and monitor connector are advantageously configured to be straightforwardly and efficiently joined with and detached from one another. Embodiments of sensor and monitor connectors having similar connection mechanisms are described in U.S. patent application Ser. No. 12/248,856 (hereinafter referred to as "the '856 Application"), filed on Oct. 9, 2008, and published as U.S. Patent Application Publication No. 2009/0099423, which is incorporated in its entirety by reference herein. For example, the sensor connector 203 includes a mating feature 213 which mates with a corresponding feature (not shown) on the monitor connector. The mating feature 213 may include a protrusion which engages in a snap fit with a recess on the monitor connector. In certain embodiments, the sensor connector 203 can be detached via one hand operation, for example. Examples of connection mechanisms which are incorporated by reference herein may be found specifically in paragraphs [0042], [0050], [0051], [0061]-[0068] and [0079], and with respect to FIGS. 8A-F, 13A-E, 19A-F, 23A-D and 24A-C of the '856 Application, for example, which is part of the incorporated disclosure thereof. The sensor system 200 measures one or more physiological parameters of the patient, such as one of the physiological parameters described above.

In addition, the sensor connector 203 and monitor connector 209 may advantageously reduce the amount of unshielded area in and generally provide enhanced shielding of the electrical connection between the sensor and monitor in certain embodiments. Examples of such shielding mechanisms which are incorporated by reference herein are disclosed in the '856 Application in paragraphs [0043]-[0053], [0060] and with respect to FIGS. 9A-C, 11A-E, 13A-E, 14A-B, 15A-C, and 16A-E, for example, which again is part of the incorporated disclosure thereof.

FIG. 2 also shows the disposable component 206 including a base 214, an assembly/disassembly clip 216 and a front holding clip 218, the clips each adapted to accept the emitter casing 208 and detector casing 210, respectively. In the preferred embodiment, front holding clip 218 includes a front stop 220. Front stop 220 is advantageous for a number of reasons. It helps reduce the likelihood that the reusable component 102, and in particular detector casing 210, will slide forward in the front holding clip 218 during assembly or use. In addition, in an embodiment where the stop 220 comprises plastic or other liquid resistant material, the stop 220 provides a liquid resistant connection between the detector casing 210 and front holding clip 218, reducing the likelihood of sensor contamination and electrical shorts. Rubber or a similar material may be used in an embodiment to compose such a front stop 220.

Figure 3A:
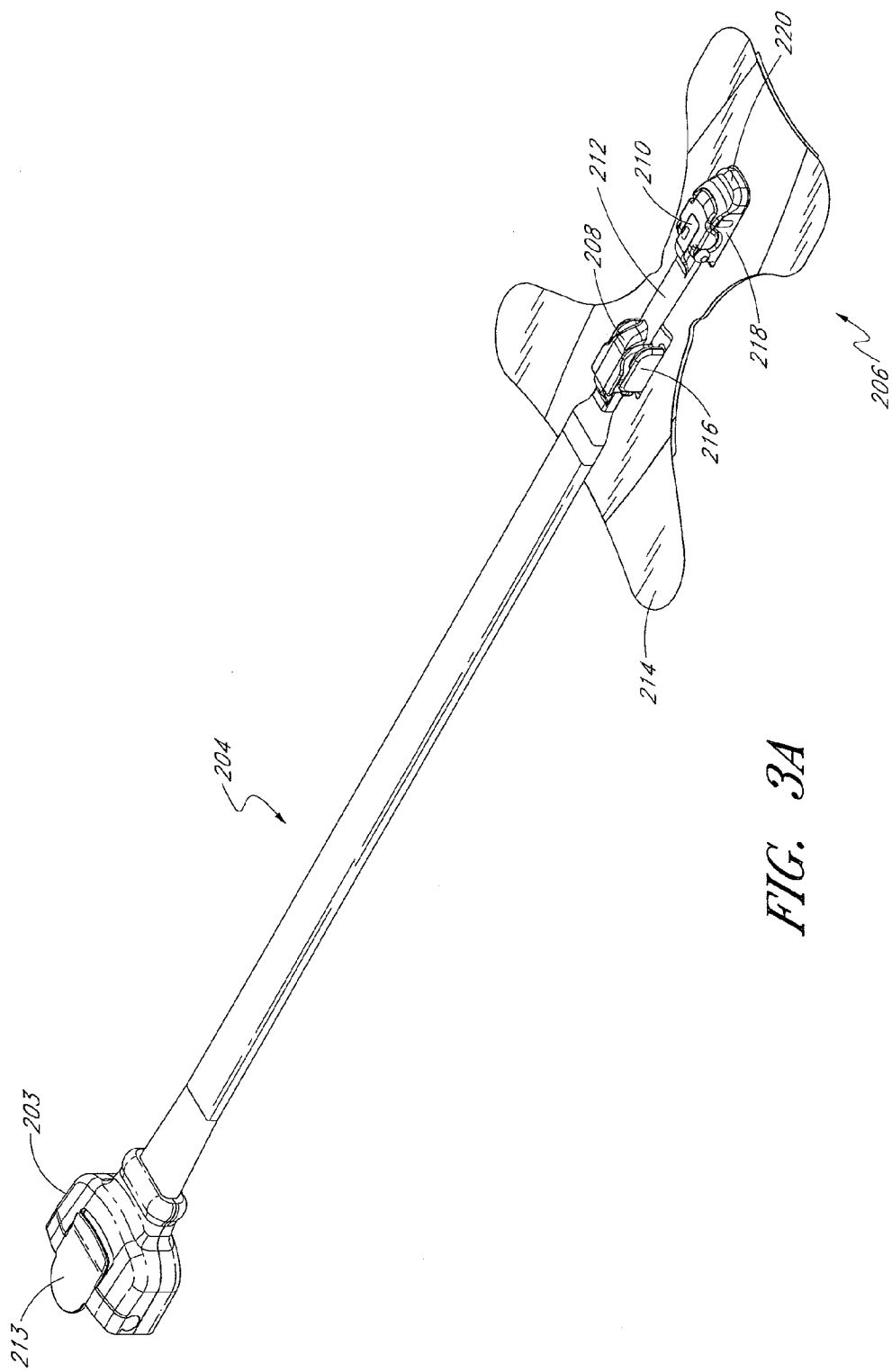
FIGS. 3A-3B illustrate perspective views of the sensor of FIG. 2, where the components are connected in an assembly/disassembly position, according to an embodiment of the disclosure.

FIG. 3A shows detector casing 210 clipped or snapped into front holding clip 218. In an embodiment, a protrusion 211 (FIG. 5A) on a tip of the casing 210 mates with a corresponding recess (not shown) on the front stop 220. While shown as a circular protrusion 211 and a circular recess, the components may include a variety of shapes such as, for example, rectangular, square, triangular and the like. Moreover, in other embodiments, the components may be reversed and the holding clip 218 may include a protrusion 211 and the casing 210 may include the recess. An artisan will recognize from the disclosure provided herein that any mechanically mating or male-female like mechanical connection, or reversals thereof may assist in guiding the casing 210 into the clip 218. This allows the front stop 220 to reduce horizontal movement of the detector casing 210, and helps reduce vertical release of the detector casing unless pulled from, for example, the cable. In another embodiment, a tip of the casing 210 may slide below a portion of the front stop 220, such as, for example, a generally hooded portion (not shown) of the front stop 220. FIG. 3 also shows the front stop 220 with a generally rounded shape and including few, if any, sharp edges. Such an embodiment advantageously reduces damage to a patient or the sensor if the patient tries to scratch body tissue using the edges of the assembled sensor, or if the sensor is dropped, banged against something while worn, or the like. This is particularly useful when used with burn victims or other patients whose skin may damage easily.

Figure 3B:
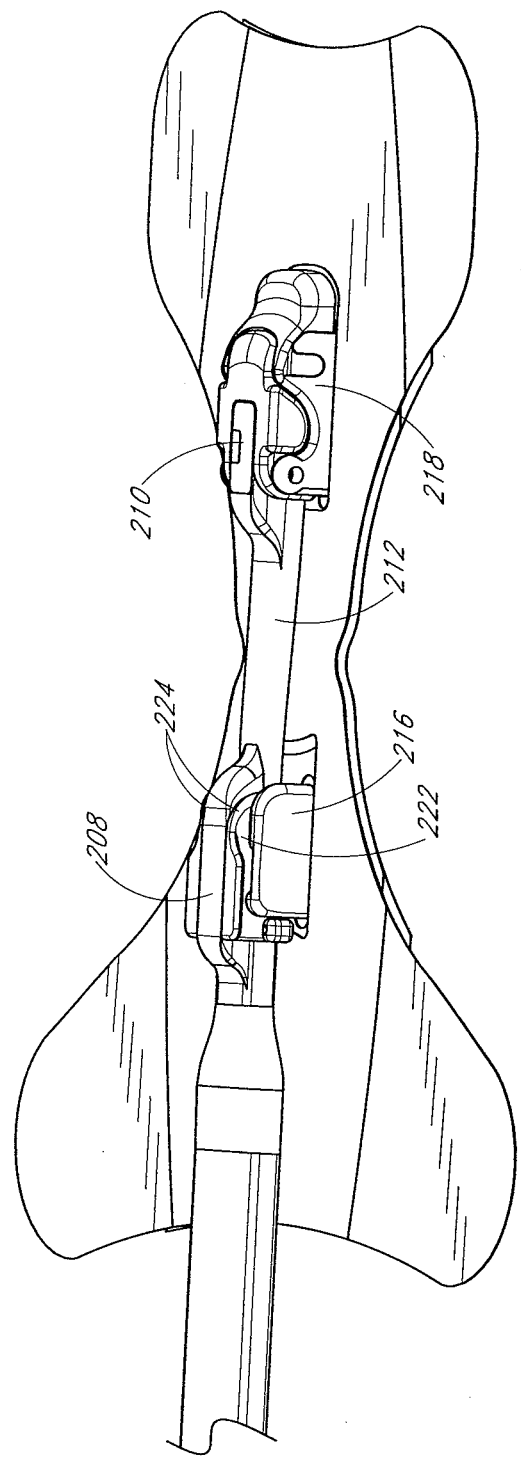

FIG. 3B highlights the ease of assembly. The disposable portion 206 is set on a surface or held in the one hand. The caregiver then aligns a front tip of casing 210 and guides it into front holding clip 218. The casing 210 including rounded wings 531 (FIG. 5) that mechanically associate with rounded side walls 739 (FIG. 7). These mechanical structures allow the casing 210 to slide and/or snap into place. Once casing 210 is in place, casing 208 aligns vertically and simply slides down, with tabs 262 (FIG. 6) sliding into slots 222 (FIG. 8) on a side of assembly/disassembly clip 216. In an embodiment, the flexible circuit portion 212 between the casings 208 and 210 may bulge slightly.

Figure 4:
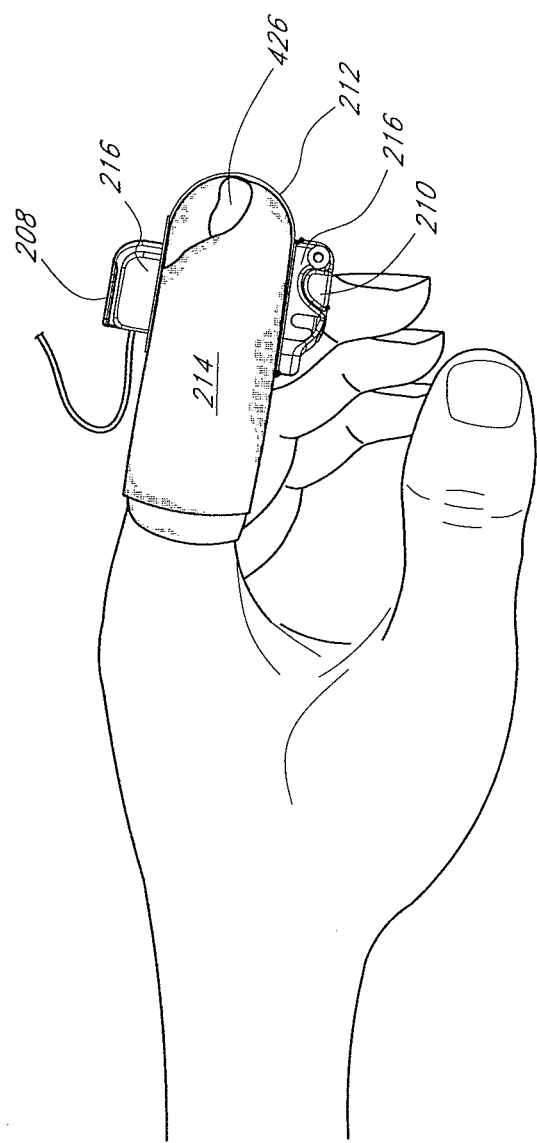
FIG. 4 illustrates a perspective side view of the sensor of FIG. 2, where the components are in an attached position, according to an embodiment of the disclosure.
Figure 8:
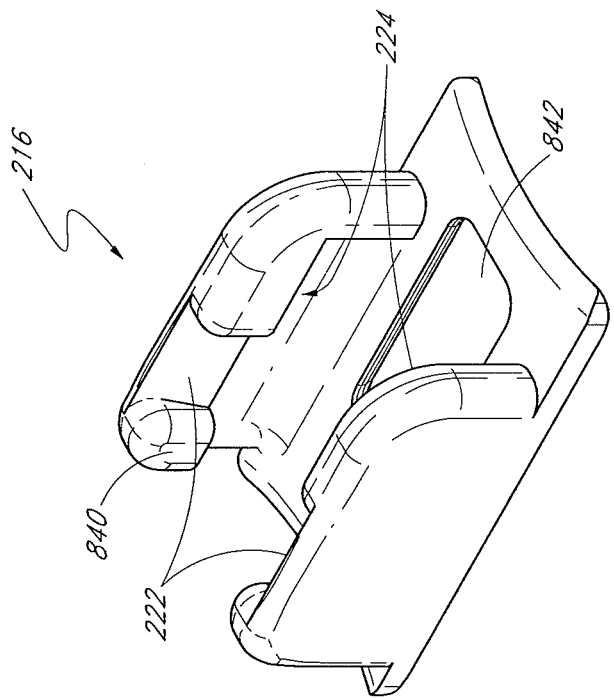
FIG. 8 illustrates a perspective view of the assembly/disassembly clip of the disposable component, the clip being capable of mechanically mating with the emitter casing of FIG. 6, according to an embodiment of the disclosure.

FIG. 3B shows the emitter casing 208 after it has been slid onto assembly/disassembly clip 216. With the reusable sensor component 204 and the disposable sensor component 206 in a generally flat position and unattached position, the emitter casing 208 remains vertically mobile up through slots 222 of assembly/disassembly clip 216 and horizontally mobile through holding regions 224. When the sensor 102 is wrapped around a measurement site 426, such as a finger, as shown in FIG. 4, emitter casing 208 slides forward in assembly/disassembly clip 216 due to the tension from flexible circuit 212 and detector casing 210 being substantially immobile in front holding clip 218. Tabs 262 (FIG. 6) slide away from their original positions underneath slots 222 (FIG. 8) to positions within the holding regions 224 (FIG. 8). Holding regions 224 prevent emitter casing 208 from moving vertically or further forward by restricting tabs 262. As stated before, the tension from flexible circuit 212 when it is wrapped around a measurement site 426 prevents the emitter casing 208 from moving horizontally backwards when wrapped around a measurement site. The immobility of casing 210, combined with the tabs 262 sliding away from underneath the slots 222 to within the holding regions 224, effectively secure the reusable sensor component 204 with respect to disposable component 206, with the emitters appropriately position with respect to the detector. Thus, realignment through release of tension, i.e., removing the sensor from an attachment site and straightening it out, ensure straightforward disassembly of the sensor components. Although shown using tabs 262 and slots 222, a skilled artisan will recognize from the disclosure herein a wide variety of mechanical mechanisms that ensure reliable attachability when the sensor is applied to the tissue site and straightforward assembly/disassembly when the sensor is removed. For example, one or more detents that snap closed beyond a catch and are released through pinching could be used to secure the reusable portion 104 to the disposable portion 106.

As alluded to previously, FIG. 4 depicts sensor 102 as would be seen when in use on a measurement site 426. In this case, the measurement site is a finger, but other sites such as a toe, ear, wrist or ankle may also work. Disposable component 206 and reusable component 204 are attached, and reusable component 204 is in the assembled and attached position. Longitudinal tension on the flexible circuit 212 from the differing radius between the tape and the flex circuit has pulled the emitter casing 208 forward, placing tabs 262 within the holding regions 224. FIG. 4 shows that, in an embodiment, emitter casing 208 is rearward with respect to assembly/disassembly clip 216 when in the unattached position (FIG. 3B), but the front of emitter casing 208 is forward with respect to the assembly/disassembly clip 216 when in the attached position (FIG. 4).

Figure 5A:
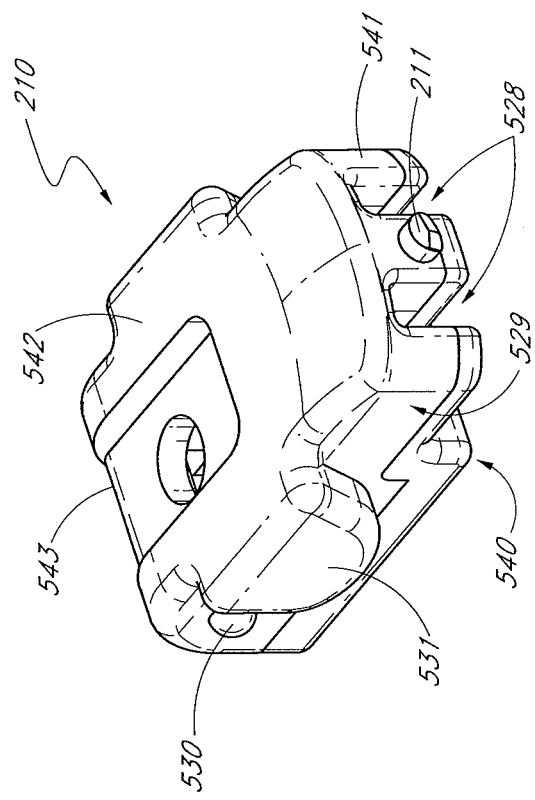
FIGS. 5A-5B illustrate top and bottom perspective views of a detector casing or housing of the reusable component, according to an embodiment of the disclosure.
Figure 5B:
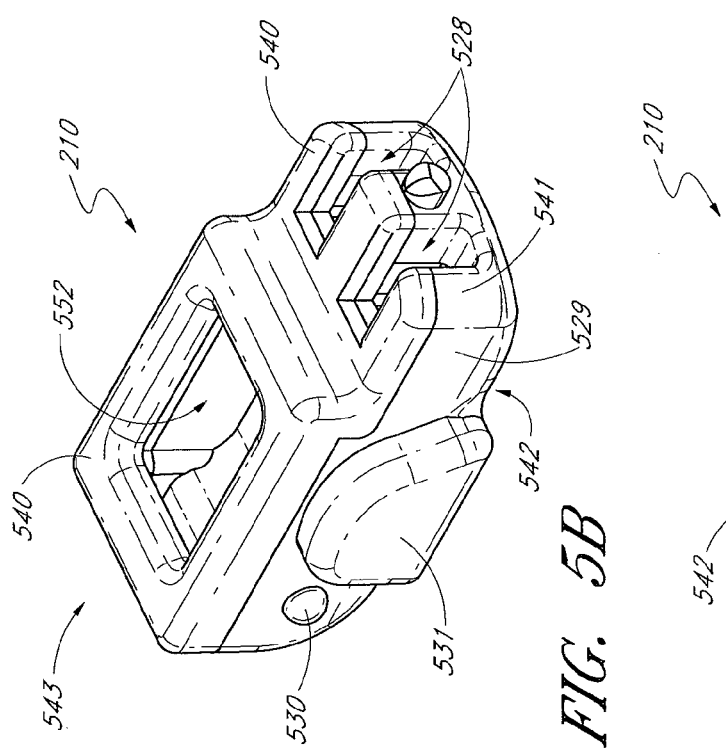
Figure 5C:
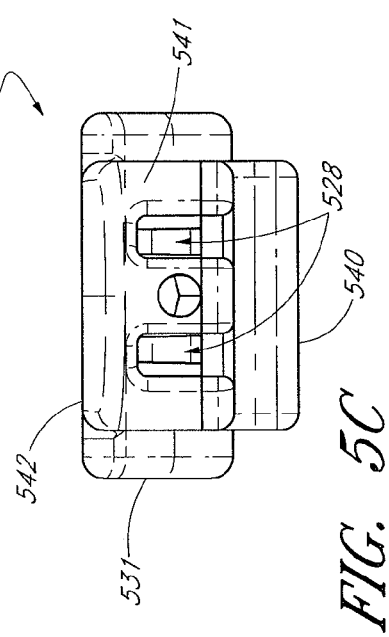
FIG. 5C illustrates a front view of a detector casing or housing of the reusable component, according to an embodiment of the disclosure.

FIGS. 5A-5C show close up top and bottom perspective and front views of an embodiment of the detector casing 210, respectively. The detector casing 210 includes bottom 540, front 541, top 542 and rear 543 surfaces. The detector casing 210 includes electrical contact acceptors 528. In an embodiment, electrical contact acceptors 528 extend along a portion of the bottom 540 and along a portion of the front 541 of the detector casing 210. The electrical contact acceptors 528 may also be referred to as openings 528 and include conductive material that can be connected to a wire in flexible circuit 212. As shown, the front portion 529 of the detector casing 210 may include a cutout such that front portion 529 sits on a raised step 733 portion of the front holding clip 218 (see FIG. 7). Buttons 530 found on a side of the detector casing 210 are, in the preferred embodiment, generally hemispherical protrusions adapted to sit in depressions or holes 738 found on front holding clip 218 (see FIG. 7). The detector casing 210 further includes opening 552 (FIG. 5B). The detector casing 210 can be configured to cooperate with opening 732 (FIG. 7) of the front sensor clip 218 to allow light attenuated by the patient's tissue to reach the detector electronics (not shown) housed by the detector casing 210. In various embodiments, the opening 552 can be substantially rectangular, as shown, or, alternatively, substantially circular, ovular, or some other shape.

FIG. 7 shows a close up perspective view of an embodiment of the front holding clip 218, again to show detail less easily seen in smaller figures. While most of the front sensor clip 218 may be made of plastic or some other rigid material, the preferred embodiment has front stop 220 made of plastic as has been discussed. Opening 732 is also shown here and may be a hole through front holding clip 218 or may include generally transparent material that will allow light from the LEDs to enter the tissue at the measurement site and allow light energy to be read by the photodiode. Having window 732 be transparent material will allow the sensor to obtain readings while keeping the LEDs and photodiode from becoming contaminated. Other optical filters or the like could also be housed in window 732. Additionally, in various embodiments, a transparent material, optical filter or other covering may be provided to one or more of the opening 552 of the detector casing 210, opening 662 of the emitter casing 208 and opening 842 of the rear sensor clip 216. In yet other embodiments, one or more of the various openings 552, 662, 742, 842 may comprise more than one opening.

Located inside front stop 220 are conducting prongs 734. Conducting prongs 734 are adapted to fit into electrical contact acceptors 528. In an embodiment, the conducting prongs 734 close the circuit with the information element 136. When the detector casing 210 clips into the front holding clip 218 and front stop 220, the conducting prongs 734 slide into electrical contact with acceptors 528. The completed circuit allows the sensor 102, and in turn an oximeter, to communicate with information element 136. In an embodiment, the openings 528 of the detector casing 210 receive and generally snap onto the conducting prongs 734 of the front holding clip 218. Moreover, because the openings 528 extend along a portion of the bottom 540 of the casing and along a portion of the front 541 of the casing 210, the conducting prongs 734 of the front stop 220 can attach to and release from the openings via the underside 540 of the casing 210 (e.g., due to upward pulling by the patient or medical personnel), the front 541 of casing 210 (e.g., due to lateral pulling) or angularly through both the underside 540 and the front 541 of the casing 210. Such configurations thereby allow for efficient, straightforward attachment and release of the forward casing 210. In addition, in certain embodiments, the at least one opening 528 of certain embodiments is configured to receive one or more of the prongs 734 such that the at least one prong 734 is slidable within the opening 528 during mating of the disposable attachment and the second casing 210. As shown, the at least one opening 528 may comprise a channel extending along one or more surfaces of the second casing 210, such as along a portion of a bottom surface 540 of the second casing 210 and a portion of the front surface 541 of the second casing 210. Depressions or holes 738 are located on the interior of front holding clip 218. They are preferably generally hemispherical depressions similar in size to buttons 530, so as to accept buttons 530, and hold detector casing 210 in a substantially immobile position relative to front holding clip 218. Thus, a straightforward snap-in snap-out friction fit is accomplished using buttons 530 and depressions 738.

Figure 6A:
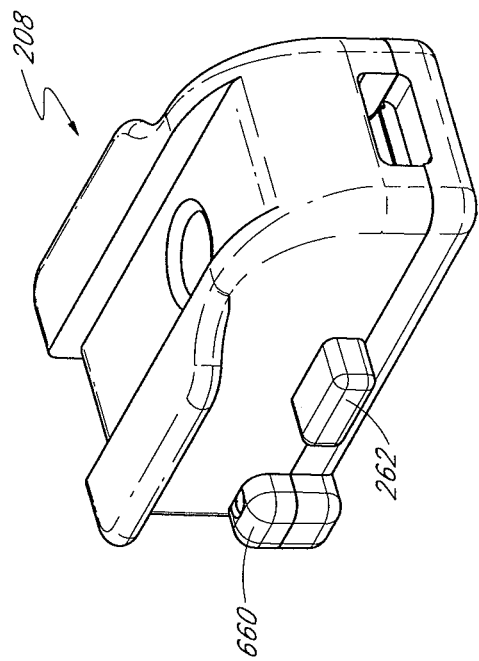
FIGS. 6A-6B illustrate top and bottom perspective views of an emitter casing or housing of the reusable component, according to an embodiment of the disclosure.
Figure 6B:
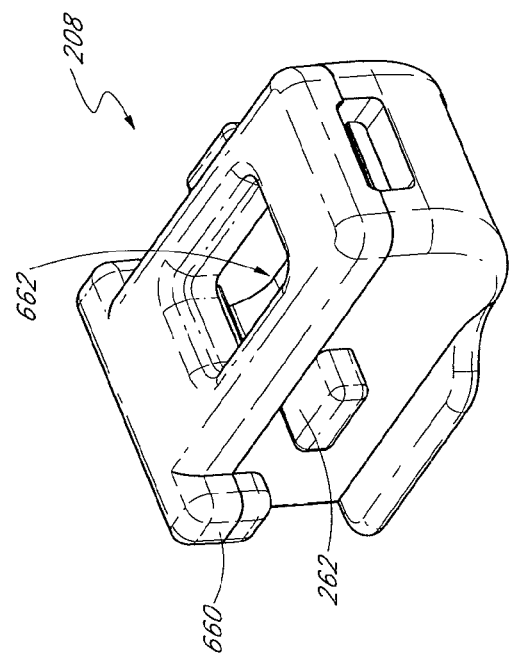
Figure 7:
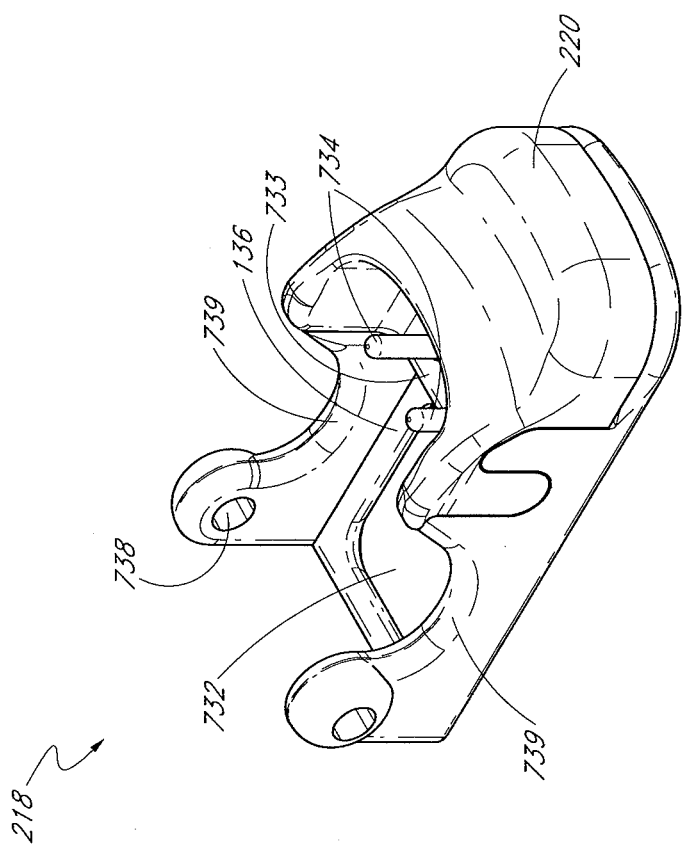
FIG. 7 illustrates a perspective view of a front holding clip of the disposable component, the clip being capable of mechanically mating with the detector casing of FIG. 5, according to an embodiment of the disclosure.

FIGS. 6A-6B show close up top and bottom perspective views of emitter casing 208. Rear pegs 660 are located on a side of emitter casing 208. When tabs 262 slide down slots 222 of assembly/disassembly clip 216, rear alignment pegs 660 slide down behind assembly/disassembly clip 216. Rear pegs 660 provide structural support integrity once emitter casing 208 has slid into a locking position by coming into position underneath rear portions 840 in assembly/disassembly clip 216 (See FIG. 8). The emitter casing 208 further includes emitter casing opening 662 (FIG. 6B). The opening 662 of the emitter casing 208 can be configured to cooperate with opening 842 (FIG. 8) of the rear sensor clip 216 to allow light emitted from the emitter (not shown) housed within the emitter casing 210 to reach, for example, the patient's skin at the measurement site. In various embodiments, the opening 662 can be substantially rectangular, as shown, or, alternatively, substantially circular, ovular, or some other shape.

FIG. 8 illustrates a close-up perspective view of a assembly/disassembly clip 216 according to the preferred embodiment. As discussed emitter casing 208, slides down into assembly/disassembly clip 216 with tabs 262 passing through slots 222 and rear pegs 660 passing behind assembly/disassembly clip 216. As emitter casing 208 slides forward due to pull from application to a user, tabs 262 generally restrict over-forward movement or any vertical movement by abutting the surface of the clip 216 above holding regions 224. Assembly/disassembly clip 216 also has a window 842 that may be, for example, substantially similar to window 732 on the front holding clip 218.

Figure 9:
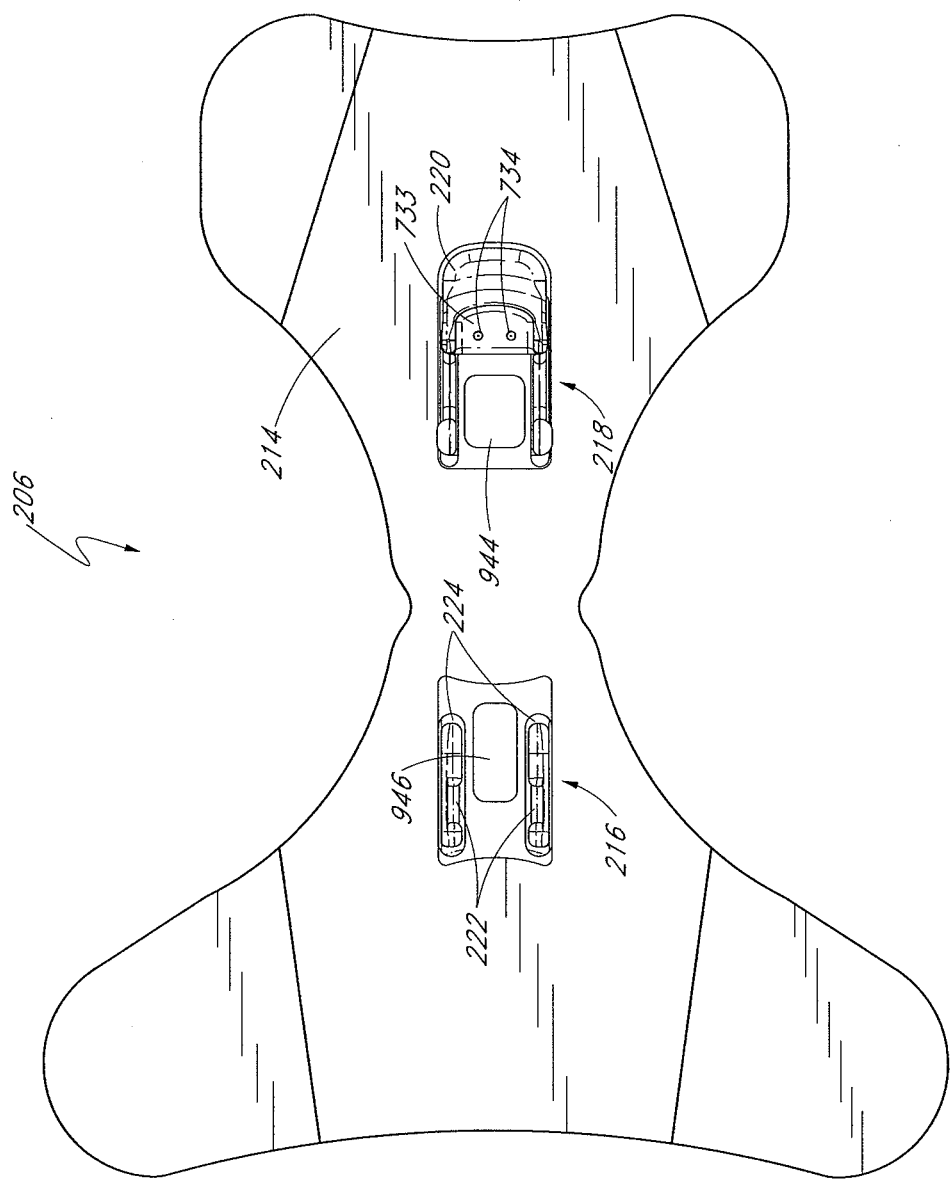
FIG. 9 illustrates a top planar view of the disposable component including the front holding clip and the assembly/disassembly clip of FIGS. 7-8, according to an embodiment of the disclosure.

FIG. 9 shows a top down view of the disposable sensor element. As shown in FIG. 9, the assembly/disassembly clip 216 and the slots 222 allow vertical entry of the tabs 262 and the emitter casing 208. Moreover, FIG. 9 shows windows 842 and 732 in assembly/disassembly clip 216 and front holding clip 218, respectively. FIG. 9 also shows windows 944 and 946. Windows 944, 946 are included in the base 214. Like the openings 732, 842, windows 944, 946 may be holes through base 214, or they may be of a material allowing free light transmission. Windows 944, 946 generally align with one or more of the openings 552, 662, 732 and 842 to provide optical access to the measurement site for the emitters and detectors of the sensor. FIG. 9 also shows the contact prongs 734 on the insides of front stop 220. The contact prongs of the illustrated embodiment are positioned on the raised step portion 733 of the holding clip 218. The contact prongs 734 connect the reusable sensor component 204 to the information element 136, which may be variously utilized such as for storing information relating to the sensor's manufacturer or the like.

Manufacture

Figure 10A:
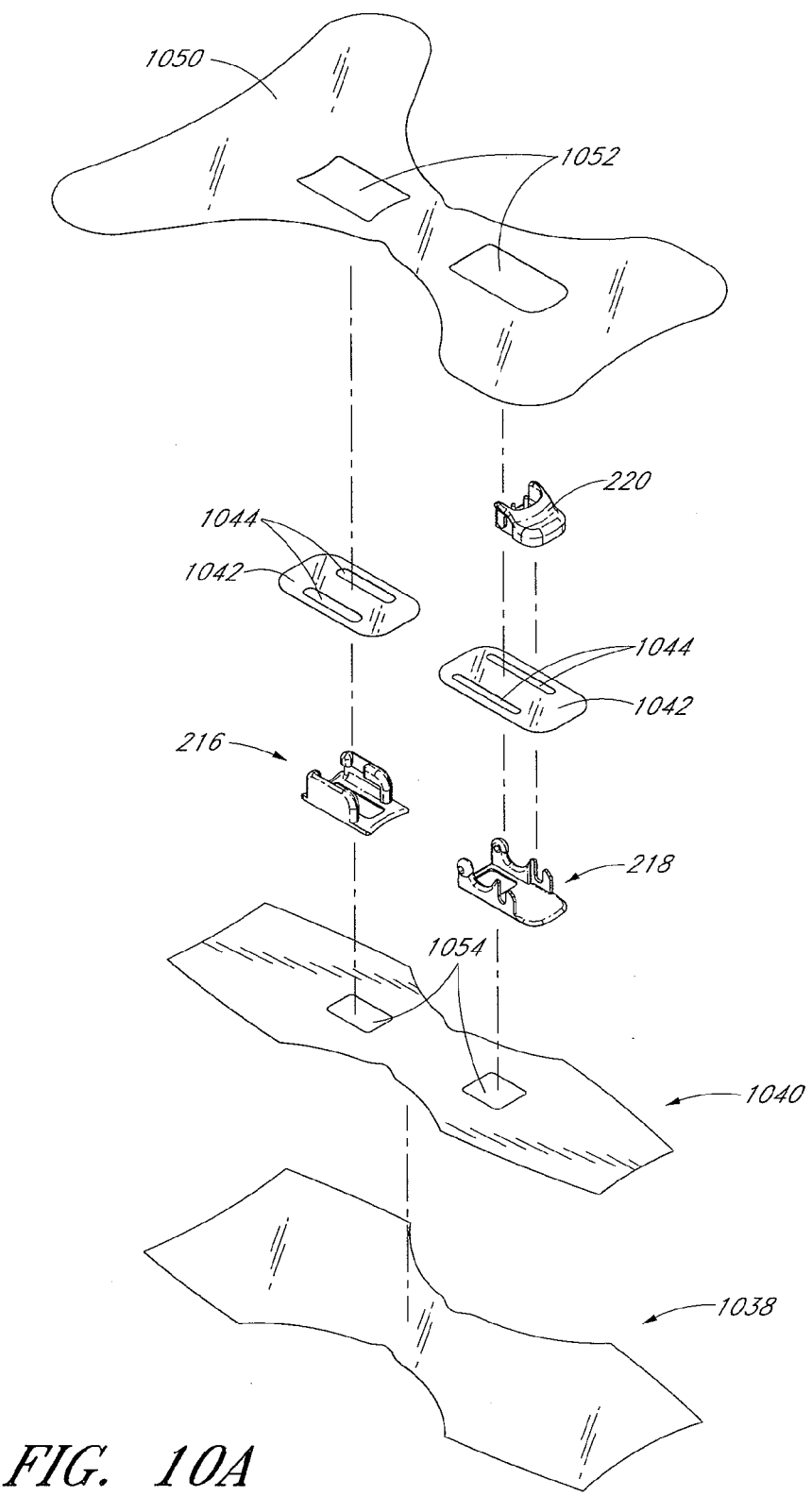
FIG. 10A illustrates an exploded view of the disposable component, according to an embodiment of the disclosure.

FIG. 10A illustrates an exploded view of an embodiment of disposable sensor component 206. As shown in FIG. 10A, disposable sensor component 206 comprises a plurality of layers. For example, disposable sensor component 206 includes a base tape 1038. This base tape 1038 is preferably transparent polyethylene approximately 0.001 inches thick. Such material can be purchased from various sources, such as Product Number 3044 from Avery Dennison Medical of 7100 Lindsey Dr., Mentor, Ohio, 44060. As with all dimension recitations herein, an artisan will recognize from the disclosure herein that the dimensions of a particular layer may advantageously be redesigned according to various design desires or needs, and layers may be added or combined without departing from the scope of the present disclosure.

A second layer comprises a tape or web layer 1040. This layer is preferably white polypropylene also approximately 0.001 inches thick. One potential source for this material is Scapa North America, 540 North Oak Street, Inglewood, Calif., 90302, specifically product number P-341. Tape layer 1040 also has windows 1054 that allow light energy emanating from the sensor emitters to pass through this layer to the measurement site 426 and also allows the light to pass through to the detector. The windows 1054 may be holes, transparent material, optical filters, or the like. In the preferred embodiment, base tape 1038 does not have windows 1054. Base tape 1038 is preferably generally clear as discussed above. This allows light to pass through the tape from the sensor, while also generally reducing contamination of the sensor components. Disposable component 206 also includes clip 218 and assembly/disassembly clip 216. In an embodiment, a pair of polyester film segments 1042 sandwich the clips 216, 218 in place. In an embodiment the polyester film segments 1042 are generally clear and approximately 0.003 inches thick. Polyester film segments 1042 also include slots 1044 to allow the vertical elements of assembly/disassembly clip 216 and front holding clip 218 to protrude therefrom and to allow polyester film segments 1042 to sit relatively flatly against the bases of assembly/disassembly clip 216 and front holding clip 218. In other embodiments, the polyester film segments 1042 include one integral segment or more than two separate segments. Front stop 220 may be connected to the vertical elements of front holding clip 218 with polyester film segments 1042 therebetween. In an embodiment, information element 136 resides within front stop 220, preferably affixed in place by adhesives and/or mechanical structure. For example, the front stop 220 may house the information element 136 in a depression, slot or cavity of the front stop 220. Such a configuration may improve the tamper resistance so that the information element 136 is less likely to be disabled, damaged, replaced or removed, for example.

In certain embodiments, the disposable portion 206 includes a bottom liner layer (not shown). The bottom liner layer may be affixed to the underside of the base tape 1038, for example. In an embodiment, the base tape 1038 includes adhesive for attaching the disposable component 206 to the patient and the bottom liner layer is configured to peel off and expose the adhesive layer. In another embodiment, the bottom liner layer itself includes adhesive for attaching the disposable component 206 to the patient.

In other embodiments, the disposable portion 206 also includes one or more light-blocking layers. For example, the disposable portion 206 may include a first light-blocking layer preferably made of metalized polypropylene approximately 0.002 inches thick. This is a commercially available product available, for example, as Bioflex™ RX48P. The first light-blocking layer can include one or more cut-outs adapted to accept portions of the disposable portion 206 such as, for example, the assembly/disassembly clip 216 and front holding clip 218. The first light-blocking layer increases the likelihood of accurate readings by preventing the penetration to the measurement site of any ambient light energy (light blocking) and the acquisition of nonattenuated light from the emitters (light piping). In an embodiment, above the light blocking layer is an opaque branding layer also having cut-outs adapted to accept portions of the disposable portion 206 such as, for example, the assembly/disassembly clip 216 and the front holding clip 218. This branding layer may advantageously comprise manufacturer's logos, instructions or other markings. Disposable sensor component 206 also comprises face tape 1050. This face tape 1050 is preferably a clear film approximately 0.003 inches thick and may be obtained commercially through companies such as 3M (product number 1527ENP), located in St. Paul, Minn., 55144. Face tape 1050 includes cut-outs 1052 adapted to accept assembly/disassembly clip 216 and front holding clip 218. In an embodiment, branding information such as manufacturer's logos, instructions or other markings may be included on the face tape 1050 instead of or in addition to on the branding layer.

Figure 10B:
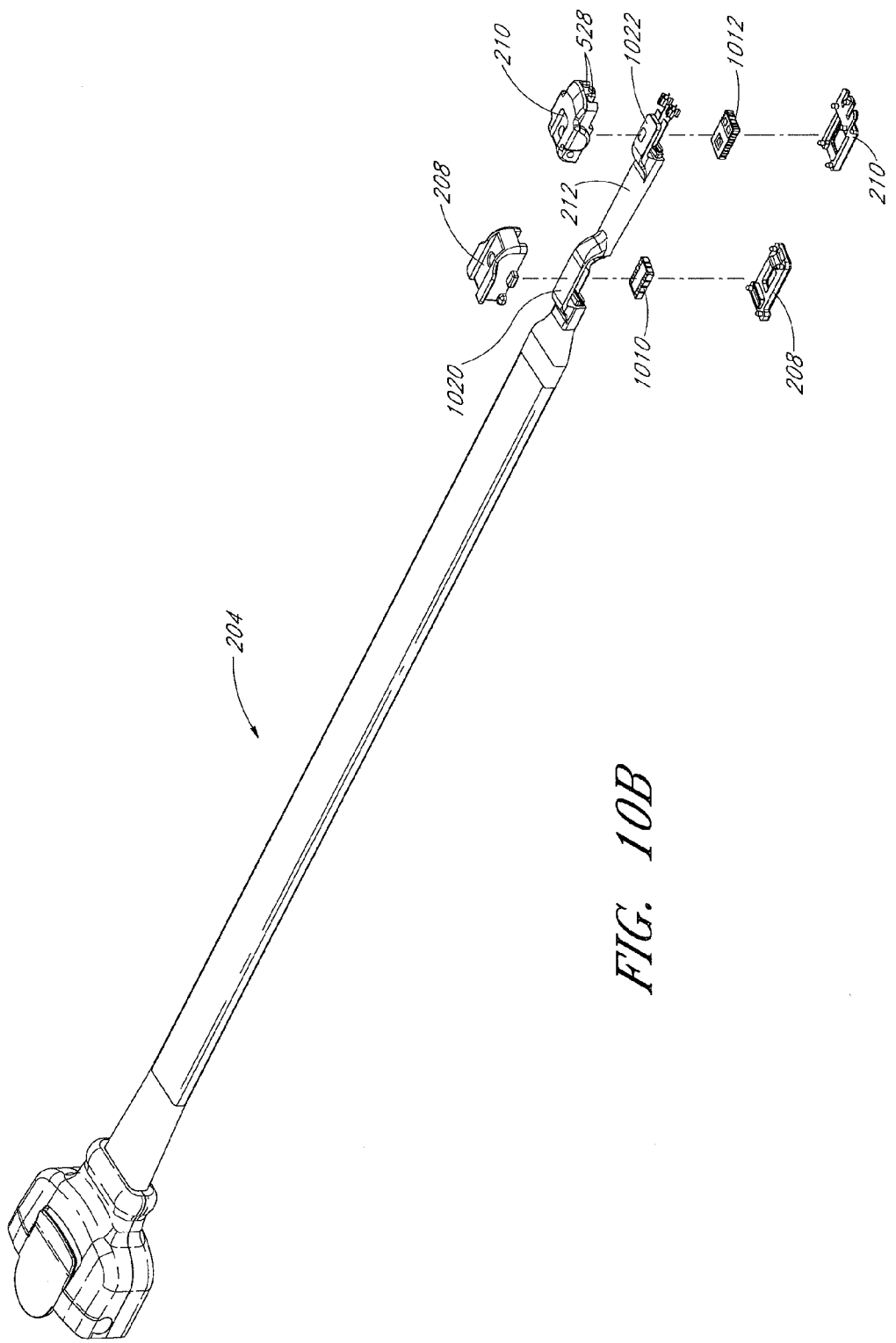
FIG. 10B illustrates an exploded view of the reusable component, according to an embodiment of the disclosure.

FIG. 10B illustrates an exploded view of a reusable component 204, according to an embodiment of the disclosure. Upper and lower portions of the emitter casing 208 mate about a portion 1020 of the reusable component 204 to enclose emitter electronics 1010. In addition, upper and lower portions of the detector casing 210 mate about a portion 1022 of the reusable component 204 to enclose detector electronics 1012. As will be appreciated by those of skill in the art from the disclosure provided herein, the emitter casing 208 and the detector casing 210 may house one or more other components such as one or more other electrical components as appropriate. For example, the detector casing 210 may include one or more wires. In another embodiment, the detector casing 210 houses one or more electrical shielding components which provide enhanced signal noise protection for the relatively sensitive detector signals.

Additional Advantages

Figure 11:
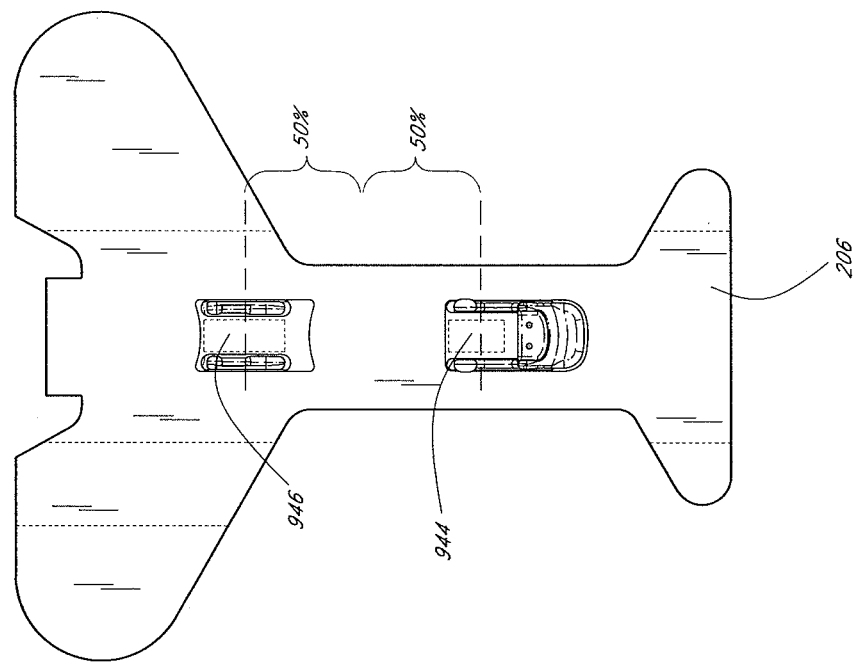
FIG. 11 illustrates top planar and side views of component placement of conventional sensors.
Figure 11:
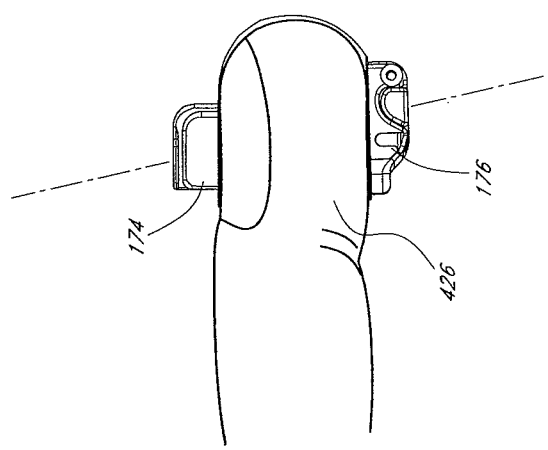

FIG. 11 illustrates a disposable sensor highlighting issues relating to sensor positioning. Generally, when applying the sensor of FIG. 11, a caregivers will split the center portion between the emitter and detector around, for example, a finger or toe. This may not be ideal, because as shown, it places the emitter 174 and detector 176 in a position where the optical alignment may be slightly or significantly off.

Figure 12:
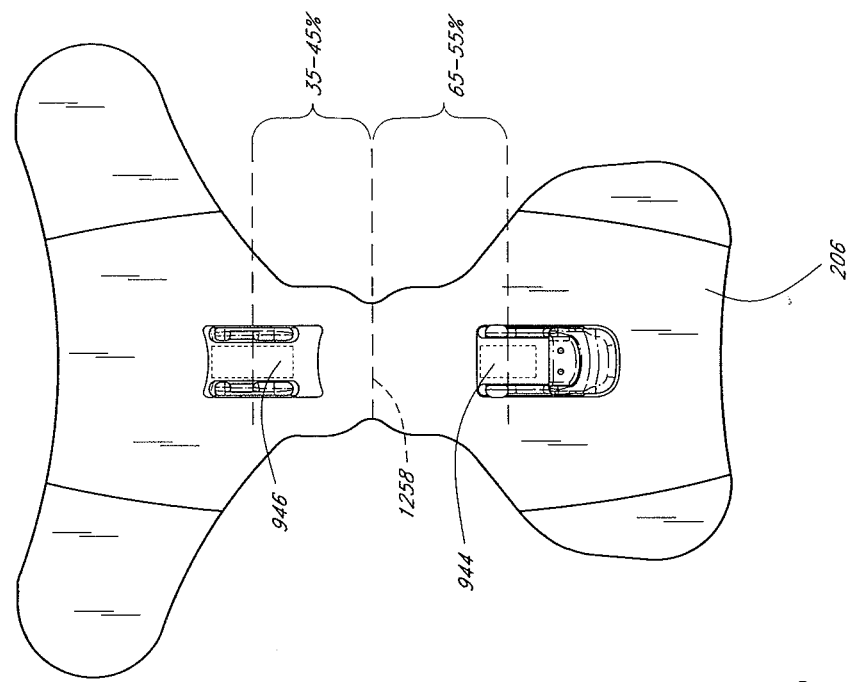
FIG. 12 illustrates top planar and side views of component placement according to an embodiment of the disclosure.
Figure 12:
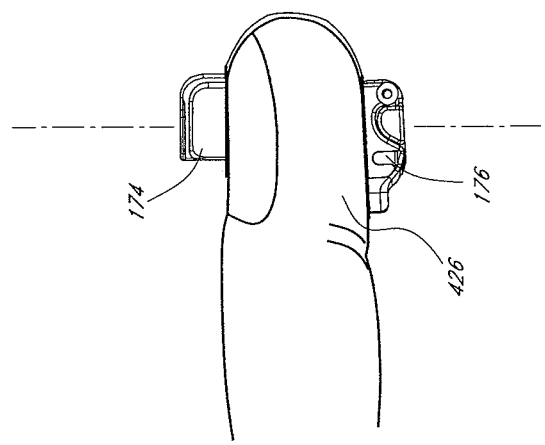

FIG. 12 illustrates an embodiment of the disposable component 206 including scoring line 1258. Scoring line 1258 is particularly advantageous, because it aids in quick and proper placement of the sensor on a measurement site 426. Scoring line 1258 lines up with the tip of a fingernail or toenail in at least some embodiments, using those body parts as the measurement site. FIG. 12 also illustrates the disposable component 206 where the distance between the windows 944, 946 is purposefully off center. For example, in an embodiment, the clips 216 and 218 will position the sensor components off center by an approximate 40%-60% split. A scoring line 1258 preferably marks this split, having about 40% of the distance from window 946 to window 944 as the distance between window 946 and the scoring line 1258. This leaves the remaining approximately 60% of the distance between the two windows 944, 946 as the distance between scoring line 1258 and window 944.

Scoring line 1258 preferably lines up with the tip of the nail. The approximately 40% distance sits atop a measurement site 426, such as the figure shown in a generally flat configuration. The remaining approximately 60% of the distance, that from the scoring line 1258 to window 944, curves around the tip of the measurement site 426 and rests on the underside of the measurement site. This allows windows 944, 946—and thus in turn detector 176 and emitter 174—to optically align across measurement site 426. Scoring line 1258 aids in providing a quick and yet typically more precise guide in placing a sensor on a measurement site 426 than previously disclosed sensors. While disclosed with reference to a 40-60 split, the off center positioning may advantageously comprise some other range such as a range from an about 35—about 65% split to an about 45—about 55% split. In a more preferred embodiment, window 944 to scoring line 1258 would comprise a distance of between about 37.5% and about 42.5% of the total distance between window 944 and 946. In the most preferred embodiment, the distance between window 944 and scoring line 1258 would be approximately 40% of the total distance between window 944 and window 946, as is illustrated in FIG. 12. With a general 40%-60% split in this manner, the emitter and detector should align for optimal emission and detection of energy through the measurement site.

Figure 13:
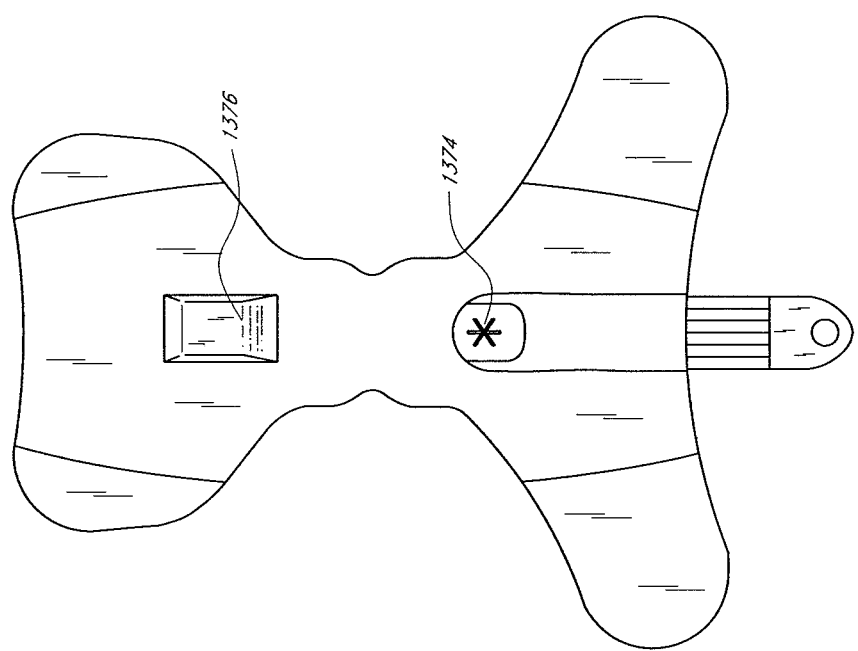
FIG. 13 illustrates a top down planar view of a disposable sensor, according to an embodiment of the disclosure.

FIG. 13 illustrates a disposable sensor containing many of the features discussed in this disclosure such as emitter 1374 and detector 1376. Based on the disclosure herein, one of ordinary skill in the art may advantageously fix the components discussed herein to form a disposable sensor without moving beyond the scope of the present disclosure.

Referring again to FIG. 2, in certain circumstances, it may be desirable to replace one or more portions of the disposable 206 or reusable 204 components of the sensor 102. For example, it may be advantageous to remove the base 214 (e.g., adhesive tape) portion from the disposable component 206, and attach a second base portion to the remaining portions of the disposable portion, such as the first receptacle 216, the second receptacle, and/or the information element (not shown). Such techniques may allow the more durable and/or expensive portions of the disposable component to be reused, reducing costs.

As such, in certain embodiments, a method of assembling a disposable attachment component of a non-invasive optical sensor is provided. The method can include providing a disposable attachment component of a non-invasive optical sensor, the disposable attachment component comprising a first flexible tape portion and at least one receptacle supported by the first flexible tape portion and for receiving at least one housing of a reusable component of the sensor. The reusable component can include at least one energy emitter and at least one detector capable of detecting energy attenuated by body tissue and capable of outputting a signal usable to determine one or more physiological characteristics of the body tissue.

The method may further include separating the first flexible tape portion from the at least one receptacle. For example, referring to FIG. 2, the base portion 214 may be cut, peeled, or otherwise separated from the remaining portion or portions of the sensor 206, such as the receptacles 216, 220.

In some embodiments, the method includes attaching a second flexible tape portion to the at least one housing such that the first flexible tape portion supports the at least one housing of the reusable component in a manner substantially similar to the manner in which the first flexible tape portion supported the reusable component. For example, referring to FIG. 2, a second base portion (not shown) may be adhered to or otherwise coupled to the receptacles 216, 220. The second base portion may be substantially similar in structure and/or function to the base portion 214, for example. Such a technique provides a re-assembled disposable component of the sensor having one or more replaced components and one or more existing components.

The first and second flexible tape portions may comprise a first aperture and a second aperture, and the method can further comprise attaching the second flexible tape portion such that the energy emitted from the at least one energy emitter passes through the first aperture and energy attenuated by body tissue passes through the second aperture.

In embodiments including an information element, it may also be desirable to update and/or replace the information element in addition to replacing the tape portion. For example, the disposable attachment component may further comprise at least one information component, which may be any of the information elements discussed herein, and can store compatibility information, use information, and the like. The method can further include separating the first flexible tape portion from the at least one information element. In various embodiments, the information element resides in, or is otherwise physically associated with one or more of the receptacles (e.g., the receptacles 216, 220 of FIG. 2, or may alternatively be physically separate from the receptacles.

In embodiments where the information element is updated, and not replaced, for example, the method can further include attaching the second flexible tape portion to the at least one information element and modifying at least a portion of memory content of the information element. For example, memory locations storing use information, compatibility information, or the like, may be modified.

Where the information element is replaced, for example, the method can include determining at least a portion of memory contents of at least one first information element, separating the first flexible tape portion from the at least one first information element, and updating a portion of memory contents of at least one second information element in response to the at least a portion of the memory contents of the at least one first information element. For example, use or compatibility information may be transferred from the first information element to the second information element. The method can further include attaching the second flexible tape portion to the at least one second information element, producing a re-assembled disposable component.

Although the sensor disclosed herein with reference to preferred embodiments, the disclosure is not intended to be limited thereby. Rather, a skilled artisan will recognize from the disclosure herein a wide number of alternatives for the sensor. For example, the emitter and detector locations may be in the opposite housings from what was discussed here. It is also possible that the assembly/disassembly clip and sensor clip would be reversed in relation to the casings into which they clip. Additionally, other combinations, omissions, substitutions and modifications will be apparent to the skilled artisan in view of the disclosure herein. Accordingly, the present disclosure is not intended to be limited by the reaction of the preferred embodiments, but is to be defined by reference to the appended claims.

Additionally, all publications, patents, and patent applications mentioned in this specification are herein incorporated by reference to the same extent as if each individual publication, patent, or patent application was explicitly incorporated.

What is claimed is:

1. A reusable component of a noninvasive optical sensor, the reusable component comprising:
   at least one energy emitter;
   at least one detector capable of detecting energy attenuated by body tissue and capable of outputting a signal usable to determine one or more physiological characteristics of the body tissue;
   a first casing housing one of the at least one energy emitter or the at least one detector, the first casing housing including at least one locking feature;
   a second casing housing the other of the at least one energy emitter or the at least one detector, the second casing housing including:
      at least one opening extending from a bottom edge of the second casing housing into at least a portion of a bottom surface of the second casing housing; and
      at least one electrical component accessible through the at least one opening and capable of electrically communicating with a corresponding electrical component of a disposable attachment of the noninvasive optical sensor; and
   a flexible portion connecting the first casing housing to the second casing housing, the flexible portion configured to provide tension to engage the at least one locking feature of the first casing housing with a corresponding locking feature of the disposable attachment in response to mating the reusable component with the disposable attachment component and applying the noninvasive optical sensor around a tissue site of a patient.

2. The reusable component of claim 1, wherein the flexible portion is further configured to provide the tension to engage the at least one locking feature of the first casing housing with the corresponding locking feature of the disposable attachment in response to being flexed.

3. The reusable component of claim 1, wherein the flexible portion is further configured to release the tension so as to un-engage the at least one locking feature of the first casing housing with the corresponding locking feature of the disposable attachment in response to the noninvasive optical sensor being removed from around the tissue site of the patient.

4. The reusable component of claim 3, wherein the flexible portion is further configured to un-flex in response to the noninvasive optical sensor being removed from around the tissue site.

5. The reusable component of claim 1, wherein the flexible portion is further configured to, further in response to applying the noninvasive optical sensor around a tissue site of a patient, the flexible portion is engaged with the disposable attachment component to align the at least one energy emitter and the at least one detector on opposing sides of the tissue site.

6. The reusable component of claim 1, wherein the at least one opening further extends into at least a portion of a second surface of the second casing housing adjacent to the bottom surface.

7. A method of using the reusable component of claim 1, comprising:
mating the reusable component with the disposable attachment component;
attaching the disposable attachment component having the first and second casing housing mated thereto to a patient such that the disposable attachment component is wrapped around a tissue site of the patient; and
activating the at least one energy emitter to emit energy into the tissue site.

8. A method of attaching to a patient a noninvasive optical sensor, the noninvasive optical sensor comprising a reusable component and a disposable attachment component, the method comprising:
providing the reusable component including:
an emitter casing housing at least one optical emitter;
a detector casing housing at least one detector configured to detect optical radiation attenuated by body tissue and output a signal usable to determine one or more physiological characteristics of the body tissue, wherein at least one of the emitter casing housing or the detector casing housing includes at least one locking feature, and wherein at least one other of the emitter casing housing or the detector casing housing includes:
at least one opening extending along at least a portion of a bottom surface and a front surface of the at least one casing housing; and
at least one electrical component accessible through the at least one opening and capable of electrically communicating with a corresponding electrical component of the disposable attachment component of the noninvasive optical sensor; and
a flexible portion connecting the emitter casing and the detector casing;
providing the disposable attachment component configured to be wrapped around and attached to a tissue site of a patient; and
mating the reusable component with the disposable attachment component,
wherein the flexible portion is configured to, in response to the noninvasive optical sensor being wrapped around the tissue site of the patient, the flexible portion provide tension to engage the at least one locking feature with a corresponding locking feature of the disposable attachment component.

9. The method of claim 8, wherein the flexible portion is further configured to flex when the noninvasive optical sensor is wrapped around the tissue site.

10. The method of claim 9, wherein flexing the flexible portion causes the at least one locking feature to engage with the corresponding locking feature of the disposable attachment component.

11. The method of claim 8, wherein the flexible portion is further configured to, in response to un-wrapping the noninvasive optical sensor from around the tissue site of the patient, release the tension to un-secure the reusable component from the disposable attachment component.

12. The method of claim 11, wherein the flexible portion is further configured to un-flex when the noninvasive optical sensor is un-wrapped from around the tissue site.

13. The method of claim 8, wherein the flexible portion includes a flexible circuit that provides communication between one of the at least one optical emitter or the at least one detector, and a patient monitor.

14. The method of claim 8, further comprising:
attaching the noninvasive optical sensor to the patient such that the disposable attachment component is wrapped around the tissue site of the patient; and
activating the at least one optical emitter to emit energy into the tissue site.

15. A reusable component of a noninvasive optical sensor, the reusable component comprising:
an emitter means for emitting optical radiation;
a detector means for detecting optical radiation attenuated by body tissue and outputting a signal usable to determine one or more physiological characteristics of the body tissue;
a first housing means for housing one of the emitter means or the detector means, the first housing means including at least one locking means;
a second housing means for housing the other of the emitter means or the detector means, the second housing means including at least one electrical communication means, wherein the second housing means is configured to:
provide at least lateral engagement and disengagement with corresponding housing of a disposable attachment of the noninvasive optical sensor; and
enable electrical communication of the at least one electrical communication means with a corresponding electrical component of the disposable attachment through at least one opening extending along at least a portion of a bottom and a front surface of the second housing means; and
a connector means for flexibly connecting the first housing means to the second housing means, the connector means configured to provide tension to engage the at least one locking means of the first housing means with a corresponding locking feature of the disposable attachment in response to mating the reusable component with the disposable attachment component of applying the noninvasive optical sensor around a tissue site of a patient.

16. The reusable component of claim 15, wherein the connector means is further configured to provide the tension to engage the at least one locking means of the first housing means with the corresponding locking feature of the disposable attachment in response to being flexed.

17. The reusable component of claim 15, wherein the connector means is further configured to release the tension so as to un-engage the at least one locking means of the first housing means with the corresponding locking feature of the disposable attachment in response to the noninvasive optical sensor being removed from around the tissue site of the patient.

18. The reusable component of claim 17, wherein the flexible connector means is further configured to un-flex in response to the noninvasive optical sensor being removed from around the tissue site.

* * * * *

UNITED STATES PATENT AND TRADEMARK OFFICE
CERTIFICATE OF CORRECTION

PATENT NO. : 9,138,182 B2
APPLICATION NO. : 14/066529
DATED : September 22, 2015
INVENTOR(S) : Ammar Al-Ali Page 1 of 1

It is certified that error appears in the above-identified patent and that said Letters Patent is hereby corrected as shown below:

In the Specification

In column 3 at line 19, Change "the a" to --the--.

In column 5 at line 37, Change "disposable" to --Disposable--.

In column 11 at line 59, After "of" change "a" to --an--.

In the Claims

In column 17 at line 47, In Claim 8, after "patient," delete "the flexible portion".

In column 18 at line 29, In Claim 15, after "with" insert --a--.

In column 18 at line 43, In Claim 15, after "component" delete "of".

In column 18 at lines 58-59, In Claim 18, after "wherein the" delete "flexible".

Signed and Sealed this
Nineteenth Day of April, 2016

Michelle K. Lee
*Director of the United States Patent and Trademark Office*